United States Patent [19]

Coursant

[11] 4,446,739

[45] May 8, 1984

[54] ECHO ULTRASOUND EXAMINATION DEVICE WITH MULTI-LAYER TRANSDUCER

[75] Inventor: Roger-Henri Coursant, Paris, France

[73] Assignee: U.S. Philips Corporation, New York, N.Y.

[21] Appl. No.: 332,994

[22] Filed: Dec. 21, 1981

[30] Foreign Application Priority Data

Dec. 22, 1980 [FR] France .................... 80 27202

[51] Int. Cl.³ .......................................... G01N 29/00
[52] U.S. Cl. ........................................ 73/609; 73/620; 73/628; 73/641
[58] Field of Search ............... 73/620, 628, 641, 609

[56] References Cited

U.S. PATENT DOCUMENTS 4,096,756  6/1978  Alphonse ................ 73/609

FOREIGN PATENT DOCUMENTS 715143  9/1954  United Kingdom ............... 73/609

Primary Examiner—Howard A. Birmiel
Attorney, Agent, or Firm—Jack E. Haken

[57] ABSTRACT

The device comprises a transducer (1) which consists of two or more transducer layers (11) and (12) and which is connected to a transmitter circuit (2) which consists of a transmission network (21) and a control network (22) which comprises a first correction circuit (223) for the correction of the transfer function of the tranmission network (21). The transducer is furthermore connected to a receiver circuit (3) which consists of a receiver network (31) and an auxiliary network (32) which comprises a second correction circuit (323) for the correction of the transfer function of the receiver network (31). The correction circuits (223) and the (323) consist of an adder circuit with a number of inputs, each of which is connected to an output of a delay line (227i, 327i) whose input is connected to the output of an attenuator (226i, 326i).

11 Claims, 6 Drawing Figures

ECHO ULTRASOUND EXAMINATION DEVICE WITH MULTI-LAYER TRANSDUCER

FIELD OF THE INVENTION

The invention relates to an improved echo ultrasound examination device of the type which comprises a transducer with at least two transducer layers of piezo-electric material, the first layer being connectable to a transmitter circuit and the second layer to a receiver circuit. The transmitter circuit comprises a transmission network in which there are connected, in series:
a generator for recurrent electric signals;
a first adder which receives on a first input
the electric excitation signals supplied by the signal generator; and
a first amplifier whose output can be connected to the first transducer layer.
The receiver circuit comprises a receiver network in which there are connected, in series:
a second amplifier whose input can be connected to the second transducer layer;
a delay circuit;
a signal processing circuit for processing the electric signals corresponding to the echos received.

BACKGROUND OF THE INVENTION

A device of this kind is known from European Patent Application 21534. Because the transducer comprises separate transducer layers for transmission and reception, each of these layers can be optimally adapted to its function. However, it has been found that the transmitter and receiver circuits which are interconnected via the transducer can adversely interfere with one another.

It is an object of the invention to reduce such interference substantially, to uncouple the ultrasonic transmitter and receiver circuits in a suitable manner and, at the same time, to enable control of the sensitivity and attenuation of the transducer.

SUMMARY OF THE INVENTION

To this end, the device in accordance with the invention is characterized in that the transmitter circuit also comprises a control network which comprises a third amplifier whose output is connected to a first correction circuit for the correction of the transfer function of the transmission network, said first correcting circuit being connected to a second input of the first adder, there being provided signal supply means for supplying signals from a transducer layer which is not connected to the first amplifier to the third amplifier during transmission.

These steps enable optimum adaptation of the transfer function of the transmission network. Moreover, the correction circuit enables partial control of the attenuation and the sensitivity of the ultrasound transducer. In a preferred embodiment of the device in accordance with the invention, a further improvement is achieved. This embodiment is characterized in that the receiver circuit also comprises an auxiliary network which is adapted to connect the first transducer layer to the signal processing circuit and which comprises the following series-connected elements:
a second gate circuit which is connected between the output of the first amplifier and the first transducer layer;
a fourth amplifier; and
a second correction circuit for correcting the transfer function of the receiver network. A second addier is connected between the delay circuit and the signal processing circuit there whose output is connected to the input of the signal processing circuit. A first input of the second adder is connected to the output of the second correction circuit and a second input of the second adder is connected to the output of the delay circuit, the second gate circuit is adapted to connect the first transducer layer exclusively to the first amplifier during the transmission of the ultrasound signals and to connect it exclusively to the fourth amplifier during the reception of the echos.

The presence of the second correction circuit enhances the control of the attenuation and the sensitivity of the ultrasound transducer and enables the operation of the transducer, to be optimized.

BRIEF DESCRIPTION OF THE DRAWINGS

The invention will be described in detail with reference to the accompanying drawings.

DESCRIPTION OF THE PREFERRED EMBODIMENTS

Figure 1:
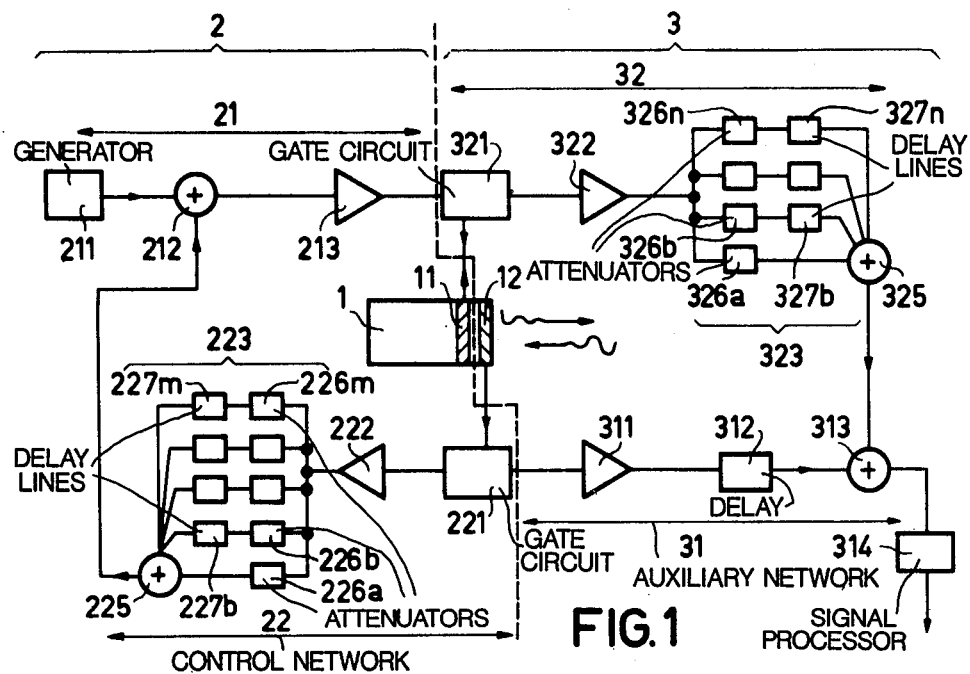
FIG. 1 is a block diagram of a first embodiment of the invention.

The ultrasonic examination device which is shown in FIG. 1 in the form of a block diagram comprises an ultrasound transducer 1 which alternately recurrently emits ultrasound signals into the object to be examined and, during the intervals between the recurrent emissions, receives echos of these signals which are returned to the transducer from the object examined.

The transducer 1 of the present embodiment comprises two transducer layers 11 and 12 which are made of possibly different piezo-electric materials and which are intended to vibrate in the thickness direction. The first layer 11, (which is reserved mainly for transmission and is made of, for example, lead titanate zirconate), is connected to a transmitter circuit 2 which provides electric excitation signals for the transducer. The second layer 12, reserved for reception and made of, for example, lead niobate. It can be connected to a receiver circuit 3 which provides the reception and the processing of the echos.

The transmitter circuit 2 comprises a transmission network 21 and a control network 22. The transmission network 21 is formed by a series connection of a broad band generator 211 for electric signals, a first linear, broad-band, low output impedance adder 212 which receives on a first input the signals supplied by the generator 211 and on a second input the output signals of the control network 22, and a first amplifier 213 for the signals present on the output of the adder. The output of the amplifier 213 is connected to the first transducer layer 11 via a circuit 321 which will be described in detail hereinafter. The control network 22, serves to connect the second transducer layer 12 to the second input of the adder 212 during the transmission of ultrasonic signals; it comprises the following series-connected elements: a first gate circuit 221 which serves as a signal supply means, a linear, broad band amplifier 222 which has a low input impedance (referred to hereinafter as the third amplifier), and a first correction circuit 223 for correcting the transfer function of the transmission network 21.

The receiver circuit 3 comprises a receiver network 31 and an auxiliary network 32. The receiver network 31 is formed by a series connection of a second amplifier 311, a delay circuit 312, a second adder 313 and a signal processing circuit 314. The second amplifier 311 is formed by a linear broad-band amplifier which can be connected to the second transducer layer 12 via the first gate circuit 221. The delay circuit 312 is provided to take into account the fact that the echos received by the transducer layer 11 have first passed through the transducer layer 12. It thus compensates for the delay incurred by these signals in the layer 12. A first input of the second adder 313 receives the delayed output signals of the second amplifier 311 and a second input thereof receives the output signals of the auxiliary network 32. The auxiliary network 32 serves to connect the first transducer layer 11 to the second input of the second adder 313 during the reception of echos. It comprises the following series-connected elements: a second gate circuit 321, a linear broadband amplifier 322 (referred to hereinafter as the fourth amplifier), and a second correction circuit 323 for correcting the transfer function of the receiver network 31.

The described device comprising the transducer with two different transducer layers not only enables the loading of the transducer 1 by the transmitter circuit 2 and the receiver circuit 3 to be optimized, but also (a) makes available in the vicinity of the first transducer layer 11 (normally reserved for transmission) a sensor (the layer 12) which absorbs a fraction of the signals transmitted by the layer 11, thus producing a correction signal whereby the transmission network can be controlled, and, conversely, (b) makes available in the direct vicinity of the second transducer layer 12 another sensor (the layer 11) which supplies an auxiliary signal which can be applied to the signal processing circuit 314 via the auxiliary network 32 in order to correct the transfer function of the receiver network 31.

The gate circuits 221 and 321 enable the execution of such correction operations during transmission and reception. During transmission, the second gate circuit 321 connects the first amplifier 213 to the transducer layer 11, the third terminal of this circuit being connected to ground. The first gate circuit 221 then connects the second transducer layer 12 to the fourth amplifier 222, its third terminal being grounded. During reception, however, the second gate circuit 321 connects the first transducer layer 11 to the fourth amplifier 322, its first terminal then floating (i.e. without electrical connection to the first amplifier 213), the first gate circuit 221 then connecting the second transducer layer 12 to the second amplifier 311, the terminal connected to the third amplifier 222 during transmission now being connected to ground.

Figure 2A:
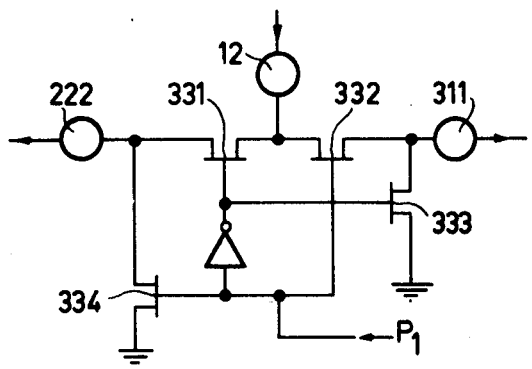
FIGS. 2a and 2b are a more detailed representation of embodiments of parts of Fig. 1.
Figure 2B:
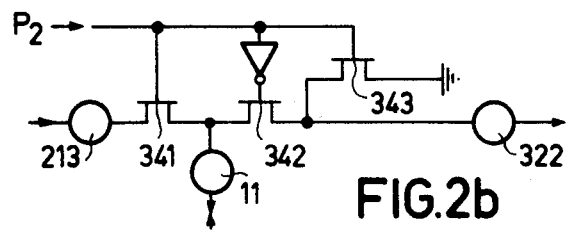
Figure 3:
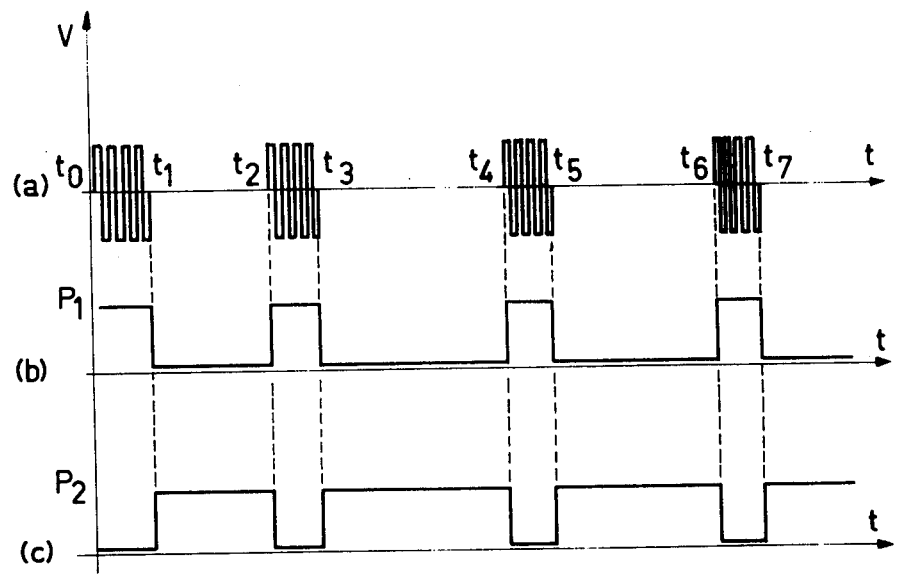
FIG. 3 shows the waveform of some signals occurring in the device shown in FIG. 1, FIG. 4 diagrammatically shows a part of a second embodiment of the invention, and FIG. 5 diagrammatically shows a part of a third embodiment of the invention.

The FIGS. 2a and 2b show embodiments of the first and the second gate circuits 221 and 321, respectively, which are controlled by the signals $P_1$ and $P_2$, respectively. These signals are shown at (b) and (c) in FIG. 3 and logic "high" or logic "low" during time intervals which are directly related to the intervals during which the electric excitation signal, being shown at (a) in FIG. 3, is supplied by the generator 211. The excitation signal consists of recurrent bursts having pseudo-periods $t_0t_2$, $t_2t_4$, etc., each burst being formed by a number of pulses which succeed one another with approximately the resonant frequency of the transducer. The periods $t_0t_1$, $t_2t_3$, etc. constitute the intervals during which transmission takes place, the periods $t_1t_2$, $t_3t_4$, etc. constituting the intervals during which reception takes place.

The three connection terminals of the first gate circuit 221 are connected to the second transducer layer 12, the third amplifier 222 and the second amplifier 311, respectively. Four field effect transistors 331, 332, 333 and 334 serve as switching members in this gate circuit. During transmission, the field effect transistors 331 and 333 are conductive and the field effect transistors 332 and 334 are blocked, the transistors 331 and 33 being blocked during reception while the transistors 332 and 334 are conductive.

The three connection terminals of the second gate circuit 321 are connected to the first transducer layer 11, the first amplifier 213 and the fourth amplifier 322, respectively. Three field effect transistors 341, 342 and 343 serve as switching elements in this gate circuit. During transmission, the field effect transistors 341 and 343 are conductive and the field effect transistor 342 is blocked, while during reception the transistors 341 and 343 are blocked and the transistor 342 is conductive.

The operation of the device during transmission and reception will be described hereinafter.

During transmission, the Laplace transform of the electric voltage present across the first transducer layer 11 is given by $$V_1(p) = A_1(p) \cdot \left[ E(p) + C_1(p) \cdot A_2(p) \cdot \frac{Z_e(p)}{Z_T(p) + Z_e(p)} \cdot V_2(p) \right]$$

In this equation, the symbols have the following meaning, where F.T. ( ... ) stands for "transfer function of ..." and T.L. ( ... ) stands for "Laplace transform of ...".

$A_1(p)$=F.T. (amplifier 213)
$A_2(p)$=F.T. (amplifier 222)
$C_1(p)$=F.T. (correction circuit 223)
$E(p)$=T.L. (excitation signal supplied by generator 211)
$V_2(p)$=T.L. (electric voltage across layer 12)
$Z_e(p)$=F.T. (input impedance of amplifier 222)
$Z_T(p)$=F.T. (impedance of layer 12)

Assuming that the bandwidth of both amplifiers 213 and 222 exceeds the width of the frequency band in which the described device operates, $A_1(p)$ and $A_2(p)$ may be considered as constants $A_1$ and $A_2$, so that:

$$V_1(p) = A_1 E(p) + C_1(p) \cdot A_2 \cdot \frac{Z_e(p)}{Z_T(p) + Z_e(p)} \cdot V_2(p)$$

If $M_1(p)=V_2(p)/V_1(p)$ and $M_2(p)=F_1(p)/V_1(p)$, in which $F_1(p)$ represents the Laplace transform of the acoustic energy generated, it follows that:

$$V_1(p) = A_1E(p) + A_1A_2\frac{Z_e(p)}{Z_T(p) + Z_e(p)} \cdot C_1(p) \cdot M_1(p) \cdot V_1(p)$$

$$V_1(p) = \frac{A_1E(p)}{1 - A_1A_2\frac{Z_e(p)}{Z_T(p) + Z_e(p)} C_1(p) \cdot M_1(p)}$$

-continued $$F_1(p) = M_2(p)V_1(p)$$

The transfer function of the closed loop is then written as:

$$\frac{F_1(p)}{E(p)} = \frac{M_2(p) \cdot A_1}{1 - A_1 A_2 \frac{Z_e(p)}{Z_T(p) + Z_e(p)} C_1(p) \cdot M_1(p)}$$

Using the so-called Cook-Redwood approximations (see the publications "Transient and steady-state response of ultrasonic piezoelectric transducers", E. G. Cook: IRE Convention Record 4, 1956, pages 61 to 69, and "Transient performance of a piezoelectric transducer", M. Redwood, Journal of the Acoustical Society of America, 33, 1961, pages 527 to 536), the following can be written:

$$\frac{Z_e(p)}{Z_T(p) + Z_e(p)} M_1(p) = K_1 \cdot \sum_{n=0}^{n=\infty} \alpha_n \cdot e^{-n\tau p} \text{ and}$$

$$M_2(p) = K_2 \cdot \sum_{n=0}^{n=\infty} \beta_n \cdot e^{-n\tau p}$$

Therein, $K_1$ and $K_2$ are transfer constants (equivalent to gain factors) and $\alpha_n$ and $\beta_n$ are functions of the reflection coefficients at the various interfaces. Due to the fast convergence of the functions $\alpha_n$ and $\beta_n$ to zero when n tends to infinite, the series in $\alpha$ and $\beta$ can be interrupted, and the following can be written:

$$\frac{F_1(p)}{E(p)} = \frac{A_1 K_2 \sum_{n=0}^{n=M} \beta_n e^{-n\tau p}}{1 - A_1 A_2 C_1(p) K_1 \sum_{n=0}^{n=M} \alpha_n e^{-n\tau p}}$$

Provided that $$A_1 A_2 C_1(p) K_1 \sum_{0}^{M} \alpha_n e^{-n\tau p}$$

is smaller than 1 (which is correct, because $K_1$ is much smaller than 1), the following is obtained by a first order approximation:

$$\frac{F_1(p)}{E(p)} = A_1 K_2 \sum_{0}^{M} \beta_n e^{-n\tau p} \left[ 1 + A_1 A_2 C_1(p) K_1 \sum_{0}^{M} \alpha_n e^{-n\tau p} \right]$$

$$\frac{F_1(p)}{E(p)} = A_1 K_2 \sum_{0}^{M} \beta_n e^{-n\tau p} +$$

$$A_1^2 A_2 K_1 K_2 C_1(p) \sum_{0}^{M} \beta_n e^{-n\tau p} \sum_{0}^{M} \alpha_n e^{-n\tau p}$$

Assuming that (by neglecting the terms having an index larger than M):

$$\sum_{0}^{M} \beta_n e^{-n\tau p} \times \sum_{0}^{M} \alpha_n e^{-n\tau p} = \sum_{0}^{M} g_n e^{-n\tau p}$$

(in which the coefficients $g_n$ are functions of $\alpha_n$ and $\beta_n$ and converge less quickly to zero than the latter), the following is obtained:

$$\frac{F_1(p)}{E(p)} = A_1 K_2 \left[ \sum_{0}^{M} \beta_n e^{-n\tau p} + A_1 A_2 K_1 C_1(p) \sum_{0}^{M} g_n e^{-n\tau p} \right]$$

If for the correction circuit 223 a circuit is chosen whose transfer function is that of an adder circuit with delay and weighting, i.e. if $C_1(p)$ can be written (in which $d_n$ are adjustable coefficients) as:

$$C_1(p) = \sum_{0}^{M} d_n e^{-n\tau p}$$

and if $\gamma_n = A_1 A_2 K_1 d_n$, the following is obtained:

$$\frac{F_1(p)}{E(p)} = A_1 K_2 \left[ \sum_{0}^{M} \beta_n e^{-m\tau p} + \sum_{0}^{M} \delta_n e^{-n\tau p} \sum_{0}^{M} g_n e^{-n\tau p} \right]$$

$$\frac{F_1(p)}{E(p)} = A_1 K_2 \sum_{0}^{M} (\beta_n + \gamma_n) e^{-n\tau p}$$

where $\sum_{0}^{M} {}_n e^{-n\tau p} \cdot \sum_{0}^{M} g_n e^{-n\tau p} = \sum_{0}^{M} \gamma_n e^{-n\tau p}$ in which, as before, the terms having an index larger than M have been neglected. Because the coefficients $\gamma_n$ can be indirectly controlled by the selection of the correction circuit 223 and the transfer function $C_1(p)$ thereof, the coefficients $\beta_n$ can be compensated for or intensified thereby in order to change the sensitivity and the attenuation of the device.

The following symbols can be introduced for the reception:

$A_3(p)$=F.T. (amplifier 311)
$A_4(p)$=F.T. (amplifier 322)
$C_2(p)$=F.T. (correction circuit 323)
$F_2(p)$=T.L. (component of the force exerted by the incident acoustic energy which is normal to the transducer)
$S(p)$=T.L. (receive signal on the output of the adder 312)
$V_1(p)$=T.L. (electric voltage across layer 11)
$V_2(p)$=T.L. (electric voltage across layer 12)
$e^{-\theta p}$=F.T. (delay circuit 312).

The following can then be written:

$$S(p) = e^{-\theta p} . A_3(p) . V_2(p) + C_2(p) . A_4(p) . V_1(p)$$

If $M_3(p) = V_1(p)/V_2(p)$ and
$M_4(p) = V_2(p)/F_2(p): V_1(p) = M_3(p). V_2(p) = M_3(p). M_4(p). F_2(p)$.

Therefore:

$$S(p) = [e^{-\theta p} . A_3(p) . M_4(p) + C_2(p) . A_4(p) . M_3(p) . M_4(p)] . F_2(p)$$

Assuming that the bandwidth of both amplifiers 311 and 322 exceeds the width of the frequency band in which the device operates, $A_3(p)$ and $A_4(p)$ may be considered to be constants $A_3$ and $A_4$. In that case:

$$\frac{S(p)}{F_2(p)} = e^{-\theta p} \cdot A_3 \cdot M_4(p) + C_2(p) \cdot A_4 \cdot M_3(p) \cdot M_4(p)$$

Using given approximations (Cook-Redwood approximations as before), the following can be written $$e^{-\theta p} \cdot M_4(p) = \sum_{0}^{M} a_n e^{-n\tau p}$$

and $M_3(p) \cdot M_4(p) = \sum\limits_{0}^{M} b_n e^{-n\tau p}$ so that $\dfrac{S(p)}{F_2(p)} = A_3 \sum\limits_{0}^{M} a_n \cdot e^{-n\tau p} + A_4 \cdot C_2(p) \sum\limits_{0}^{M} b_n e^{-n\tau p}$ If a circuit whose transfer function is again that of an adder circuit with delay and weighting is also chosen for the correction circuit 323, $C_2(p)$ will be:

$$C_2(p) = \sum_{0}^{M} c_n e^{-n\tau p}$$

so that $\dfrac{S(p)}{F_2(p)} = A_3 \sum\limits_{0}^{M} a_n \cdot e^{-n\tau p} + A_4 \sum\limits_{0}^{M} c_n e^{-n\tau p} \cdot \sum\limits_{0}^{M} b_n e^{-n\tau p}$ By ignoring the terms having an index larger than M again, the following is obtained:

$$\dfrac{S(p)}{F_2(p)} = A_3 \sum_{0}^{M} a_n \cdot e^{-n\tau p} + A_4 \sum_{0}^{M} d_n e^{-n\tau p}$$

or by writing $\alpha_n = A_3 a_n$ and $\delta_n = A_4 d_n$:

$$\dfrac{S(p)}{F_2(p)} = \sum_{0}^{M} (\alpha_n + \delta_n) \cdot e^{-n\tau p}$$

Because the coefficients $\delta_n$ can be indirectly controlled by the selection of the correction circuit 323 and the transfer function $C_2(p)$ thereof, these coefficients can again be used to compensate for or to intensify the coefficients $\alpha_n$ in order to change the sensitivity and the attenuation of the device.

The above calculations have demonstrated that the transfer functions of the transmission and receiver networks are functions of the Laplace variable, which can be formed as polynomials in $e^{-\tau p}$. The control network 22 and the auxiliary network 32 then enable the use of analog series in $e^{-\tau p}$ and to add terms in $e^{-\tau p}$, via the correction circuits included in these networks, for the purpose of correction during transmission and/or reception. These added and existing terms can be algebraically combined, i.e. added for an intensifier operation and subtracted for a cancellation operation or compensation operation.

The two correction circuits 223 and 323 in the present embodiment each comprise an adder circuit 225, 325, respectively, with a number of inputs (five inputs for the circuit 223 and four inputs for the circuit 323 in FIG. 1), each input being connected to an output of a delay line 227b to 227m and 327b to 327n, respectively, the input of which is connected to the output of an attenuator 226a to 226m and 326a to 326n, respectively. The delay lines can be formed, for example, by means of analog shift registers of the CCD (charge coupled device) type, or by using analog-to-digital converters, digital shift registers and digital-to-analog converters. A more economical solution is the search for an approximation of the delay $e^{-\tau p}$, for example, by restriction to the third order:

$$e^{-\tau p} = \dfrac{1}{e^{+\tau p}} = \dfrac{1}{1 + \tau p + \dfrac{\tau^2 p^2}{2!} + \dfrac{\tau^3 p^3}{3!}}$$

Each delay line can thus actually be a rational network having the latter expression of the polynomial type as its transfer function. Because $p = j\omega$, the series in $\tau^n p^n / n!$ is restricted to the width of the useful frequency band, i.e. in practice to the width of the spectrum of the excitation signal.

Various alternative versions of the described embodiment are feasible. The described composite transducer, for example, may alternatively comprise interference layers which are provided on the rear of the first transducer layer 11, on the front of the second transducer layer 12, and/or between these two layers. The sensitivity of the transducer and the bandwidth thereof are thus increased, so that the number of delay lines in the correction circuits 222 and 323 can be reduced.

Figure 4:
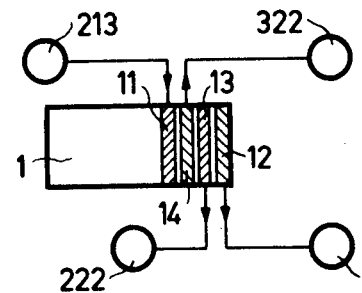
Figure 5:
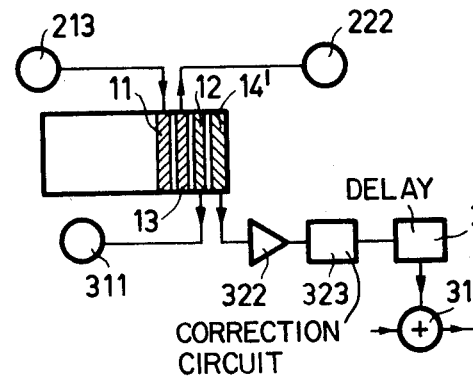

One of the gate circuits 221 and 321 (or both) can be saved at the expense of a more complex construction of the transducer. Examples thereof are diagrammatically shown in the FIGS. 4 and 5. In both cases the signal supply means for the control circuit 22 are formed by a third transducer layer 13 which is connected to the input of the third amplifier 222. The second transducer layer 12 is then permanently connected to the second amplifier 311. The first gate circuit 221 can then be dispensed with. The second gate circuit 321 can also be dispensed with if the transducer 1 comprises a fourth transducer layer (denoted by the reference numeral 14 in FIG. 4 and by the reference numeral 14' in FIG. 5). The fourth layer 14 is situated between the first and the second transducer layer (11 and 12) and is controlled to the input of the fourth amplifier 322 which is connected in series, in exactly the same way as shown in FIG. 1, with a second correction circuit 323 and a second adder 313 in order to form an auxiliary network.

If the fourth layer 14' (FIG. 5) is situated in front of the layers 11 and 12, the auxiliary network comprises a second delay circuit 324 which is connected between the second correction circuit 323 and the second adder 313. The difference between the delays introduced by the second delay circuit 324 and the first delay circuit 312 (FIG. 1) serves to take into account the fact that during reception the second layer 12 is reached by the echos only after they have passed through the fourth layer 14'. Consequently, these echos have incurred an additional delay.

What is claimed is:

1. In an echo ultrasound examination apparatus which comprises:
    a multi-layer transducer which includes a first active layer for transmitting ultrasound energy in response to an electrical stimulation signal and a second active layer for detecting ultrasound echos and producing electrical echo signals in response thereto;
    transmission network means which are operably connected to the first layer to supply stimulation signals thereto; and
    receiver network means which are operatively connected to the second layer to receive echo signals therefrom;
    the improvement comprising:
    control network means, having an input which is operably connected during transmission of ultrasound energy to a first signal supply layer of the transducer, which feedback a signal to correct the transfer function of the transmission network means and thus reduce interference between the transmission network means and the receiver network means.

2. The apparatus of claim 1 wherein the first signal supply layer is the second layer and further comprising first gate means which operably connect the second layer to an input of the receiver network means for reception of echos and which operably connect the second layer to the control network means for transmission of energy.

3. The apparatus of claim 1 wherein the transducer comprises a third active layer which is connected to an input of the control network means and functions as the first signal supply layer and wherein the second layer of the transducer is directly connected to an input of the receiver network means.

4. The apparatus of claim 2 or 3 wherein the transmission network means comprises:
a generator having an output for supplying electrical signals; a first adder having a first input connected to the output of the generator, a second input connected to an output of the control network means, and an output; and a first amplifier having an input connected to the output of the first adder and an output which comprises the output of the transmission network and is operatively connected to the first layer;
wherein the receiver network means comprise:
a second amplifier having an input, which is operatively connected to the second layer, and an output; a first delay circuit having an input connected to the output of the second amplifier; and signal processing means which are operatively connected to the output of the first delay circuit for producing electrical signals which correspond to the echos; and
wherein the control network means comprises a third amplifier having an input, which comprises the input of the control network, and an output and a first correction circuit having an input connected to the output of the third amplifier and an output which comprises the output of the control network.

5. The apparatus of claims 1, 2 or 3 further comprising auxiliary network means which feed a signal from a second signal supply layer in the transducer to the receiver network means to correct the transfer function of the receiver network means.

6. The apparatus of claim 4 further comprising auxiliary network means which feed a signal from a second signal supply layer in the transducer to the receiver network means to correct the transfer function of the receiver network means.

7. The apparatus of claim 6 wherein the second signal supply layer is the first active layer and the auxiliary network means comprise:
second gate means which are operatively connected to supply a signal from the first active layer to the input of the auxiliary network during reception of echos; a fourth amplifier having an input which comprises the input of the auxiliary network and an output; and a second correction circuit for correcting the transfer function of the receiver network;
and wherein the receiver network means further comprise a second adder having a first input connected to the output of the first delay circuit, an output connected to the input of the signal processor means, and a second input connected to the output of the second correction circuit.

8. The apparatus of claim 5 wherein the second signal supply layer comprises a fourth transducer layer which overlaps the first active layer and
wherein the auxiliary network means comprise a fourth amplifier having an input connected to receive signals from the fourth layer and an output; a second correction circuit, having an input connected to the output of the fourth amplifier, and an output for correcting the transfer function of the receiver network means; and a second delay circuit having an input connected to the output of the correction circuit and an output which comprises the output of the auxiliary network means; and
wherein the receiver network means comprise an adder having a first input which is operably connected to the output of the first delay circuit, a second input which is operably connected to the output of the second delay circuit, and an output which is connected to the input of the signal processing means.

9. The apparatus of claim 4, wherein the control circuit means comprise a plurality of attenuators each having an input connected to a common node which comprises the input of the control circuit and an output;
a plurality of delay lines each having an input connected to the output of a corresponding attenuator; and
an adder having a plurality of inputs each connected to the input of a corresponding delay line and an output which comprises the output of the control circuit means.

10. The apparatus of claim 6 wherein the control circuit means comprise a plurality of attenuators each having an input connected to a common node which comprises the input of the control circuit and an output;
a plurality of delay lines each having an input connected to the output of a corresponding attenuator; and
an adder having a plurality of inputs each connected to the input of a corresponding delay line and an output which comprises the output of the control circuit means.

11. The apparatus of claim 8 wherein the control circuit means comprise a plurality of attenuators each having an input connected to a common node which comprises the input of the control circuit and an output;
a plurality of delay lines each having an input connected to the output of a corresponding attenuator; and
an adder having a plurality of inputs each connected to the input of a corresponding delay line and an output which comprises the output of the control circuit means.

* * * * *